United States Patent
MacKinnon et al.

(10) Patent No.: US 6,645,217 B1
(45) Date of Patent: *Nov. 11, 2003

(54) OVER-THE-WIRE ATHERECTOMY CATHETER

(75) Inventors: Robert A. MacKinnon, Murrieta, CA (US); James A. Hantske, Murrieta, CA (US)

(73) Assignee: Advanced Cardiovascular Systems, Inc., Santa Clara, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/312,076

(22) Filed: May 15, 1999

(65) Prior Publication Data (65)

(51) Int. Cl.[7] ............................................. A61B 17/22
(52) U.S. Cl. .................... 606/170; 606/159; 606/171
(58) Field of Search ........................... 606/1, 159, 170, 606/171; 604/22, 27, 36, 37, 264, 523, 275, 279, 295, 524–526; 401/202, 243, 245, 246

(56) References Cited

U.S. PATENT DOCUMENTS

| | | | |
|---|---|---|---|
| 4,669,469 A | * 6/1987 | Gifford, III et al. | 606/159 |
| 4,781,186 A | * 11/1988 | Simpson et al. | 606/170 |
| 4,919,133 A | 4/1990 | Chiang | |
| 4,979,939 A | 12/1990 | Shiber | |
| 4,979,951 A | * 12/1990 | Simpson | 606/159 |
| 5,071,425 A | * 12/1991 | Gifford et al. | 156/294 |
| 5,087,265 A | 2/1992 | Summers | |
| 5,100,424 A | 3/1992 | Jang et al. | |
| 5,135,517 A | 8/1992 | McCoy | |
| 5,250,059 A | * 10/1993 | Andreas et al. | 606/159 |
| 5,250,060 A | 10/1993 | Carbo et al. | |
| 5,279,565 A | 1/1994 | Klein et al. | |
| 5,370,651 A | 12/1994 | Summers | |
| 5,402,790 A | 4/1995 | Jang et al. | |
| 5,512,044 A | 4/1996 | Duer | |
| 5,514,115 A | * 5/1996 | Frantzen et al. | 606/159 |
| 5,527,325 A | 6/1996 | Conley et al. | |
| 5,569,276 A | 10/1996 | Jang et al. | |
| 5,569,277 A | * 10/1996 | Evans et al. | 606/159 |
| 5,571,130 A | 11/1996 | Simpson et al. | |
| 5,593,394 A | * 1/1997 | Kanesaka et al. | 604/524 |
| 6,027,514 A | * 2/2000 | Stine et al. | 606/159 |
| 6,051,008 A | * 4/2000 | Saadat et al. | 606/170 |
| 6,266,550 B1 | * 7/2001 | Selmon et al. | 600/407 |

OTHER PUBLICATIONS

Webster's Ninth Collegiate Dictionary, pp. 704 and 1013.*

* cited by examiner

*Primary Examiner*—Gary Jackson
(74) *Attorney, Agent, or Firm*—Blakely, Sokoloff, Taylor & Zafman LLP

(57) ABSTRACT

An atherectomy catheter device includes a housing at the distal end of a substantially round housing torque cable. A cutter torque cable is disposed within the housing and includes a rotatable and translatable cutter at its distal end. The housing includes a window into which an atheroma protrudes. The cutter severs the atheroma. A nose cone attached to the distal end of the housing collects and stores severed atheroma. A stabilizing member is attached to the exterior of the housing opposite the window. A stabilizing member is disclosed including a balloon having an inflation lumen disposed within the housing. A mechanical stabilizing member is disclosed including a distal end attached to the distal end of the housing or to the nose cone, and a proximal end coupled to a stabilizing cable disposed within a cable lumen of the housing torque cable. The stabilizing cable may be advanced distally to bow the stabilizing member away from the housing and withdrawn proximally to flatten the stabilizing member against the housing, alternately urging the window side of the housing onto the atheroma and allowing it to retreat therefrom.

22 Claims, 3 Drawing Sheets

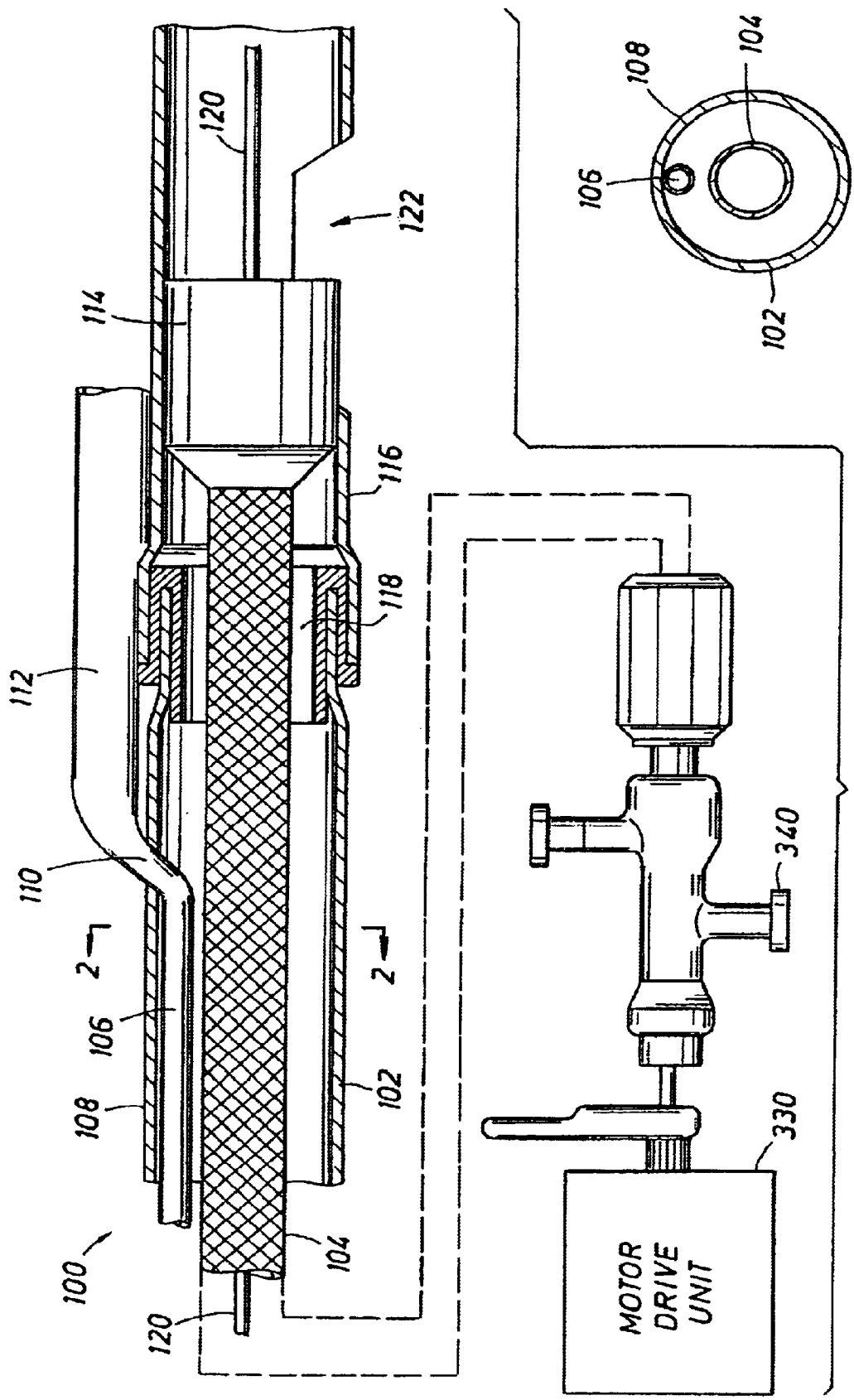

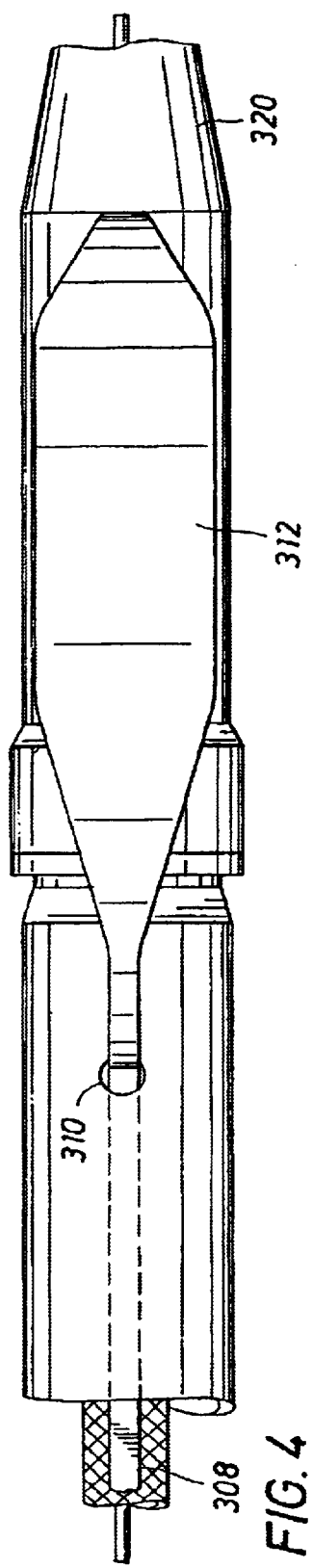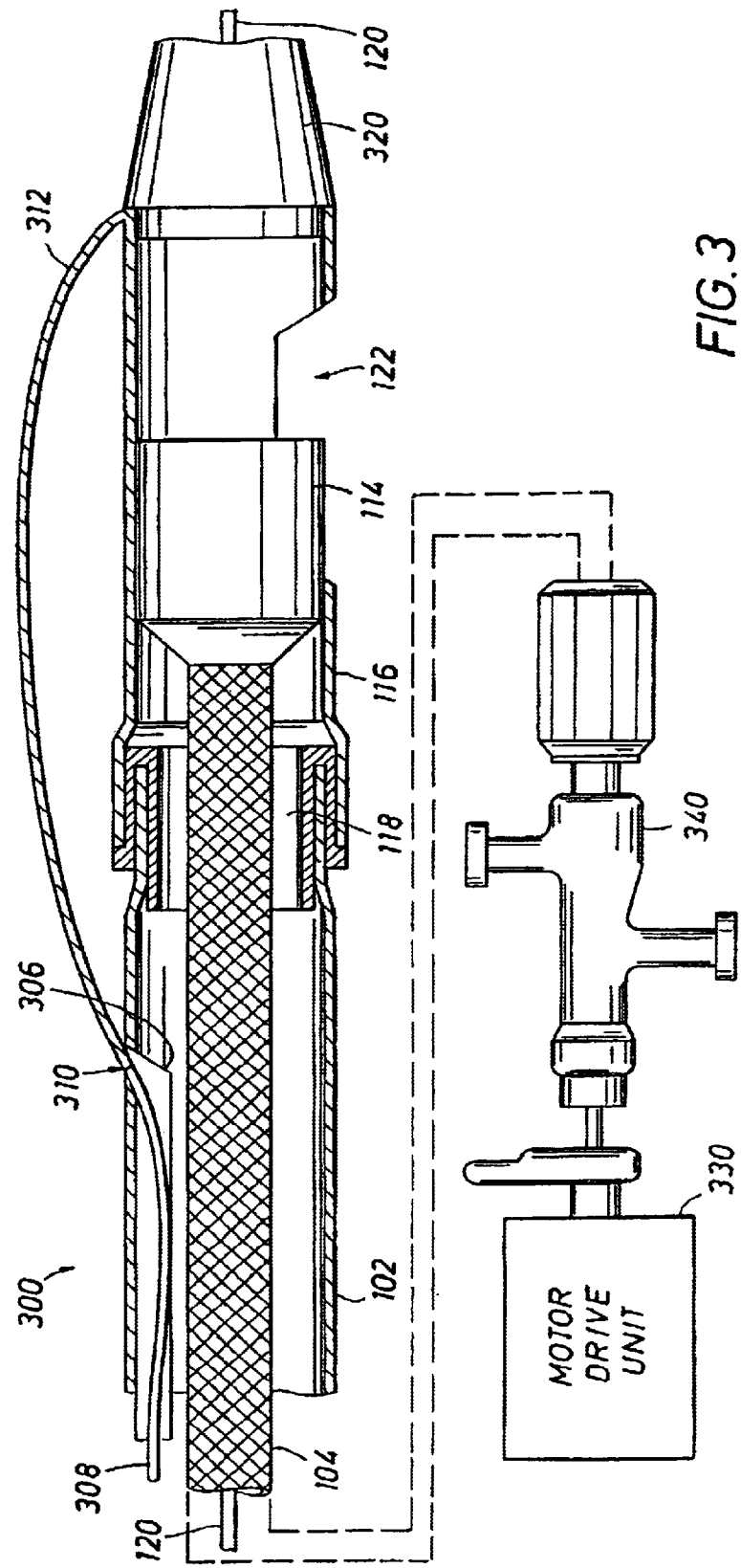
FIG. 4
FIG. 3

OVER-THE-WIRE ATHERECTOMY CATHETER

BACKGROUND OF THE INVENTION

1. Field of the Invention

This invention relates generally to catheters for performing vascular intervention surgery. More specifically, the present invention relates to catheters used in coronary atherectomy surgery.

2. Description of the Related Art

Medical science has long sought effective treatments for disease conditions involving stenosis (narrowing or obstruction) of the lumen (interior passage of the artery) of an artery. This condition, known generally as an occlusion, is found in patients suffering from atherosclerosis (accumulation of fibrous, fatty or calcified tissue in the arteries). An occlusion can manifest itself in hypertension (high blood pressure), ischemia (deficiency of circulation), angina (chest pain), myocardial infarction (heart attack), stroke or death. An occlusion may be partial or total, may be soft and pliable or hard and calcified, and may be found at a great variety of sites in the arterial system including the aorta, the coronary and carotid arteries, and peripheral arteries.

Of particular interest to cardiac medicine are the often disabling or fatal occlusions occurring in the coronary arteries (arteries supplying the heart). Traditionally, coronary artery occlusions have been treated by performing coronary bypass surgery, in which a segment of the patient's saphenous vein is taken from the patient's leg and is grafted onto the affected artery at points proximal (upstream) and distal (downstream) to the occluded segment. The bypass often provides dramatic relief. However, it entails dangerous open chest surgery and a long, painful, costly convalescence in the hospital. Moreover, with the passage of time, the patient's bypass saphenous vein graft can also become occluded. If the patient has another saphenous vein, a second bypass procedure may be performed, once again entailing open chest surgery and prolonged hospitalization. Thereafter, if the underlying atherosclerotic disease process is not controlled, the prognosis is dismal.

Newer, minimally invasive procedures are now preferred in the treatment of arterial occlusions. These procedures use a catheter, a long, thin, highly flexible device which is introduced into a major artery through a small arterial puncture made in the groin, upper arm, or neck and is advanced and steered into the site of the stenosis. At the distal end of the catheter, a great variety of miniature devices has been developed for operating upon the stenosed artery.

The more popular minimally invasive procedures include percutaneous transluminal coronary angioplasty (PTCA), directional coronary atherectomy (DCA), and stenting. PTCA employs a balloon to mechanically dilate the stenosis. In PTCA, a steerable guidewire is introduced and advanced under fluoroscopic observation into the stenosed artery and past the stenosis. Next, a balloon-tipped catheter is advanced over the guidewire until it is positioned across the stenosed segment. The balloon is then inflated, separating or fracturing the atheroma (stenosed tissue). The hoped-for outcome is that, over time, the lumen will stay open.

In directional coronary atherectomy, a catheter containing a cutter housed in its distal end is advanced over the guidewire into the stenosed segment. The housing is urged against the atheroma by the inflation of a balloon, so that part of the atheroma intrudes through a window in the side of the housing. Under fluoroscopic observation, the cutter is used to shave away the atheroma. The shavings are collected in the nose cone of the housing and withdrawn along with the catheter or flushed out of a flushing lumen running the length of the device.

All of these devices, however, suffer from one or more of the following disadvantages. The first of these disadvantages is large size. The large shaft profiles of these existing atherectomy catheters makes it necessary to use catheters of large size. This large size makes it difficult, if not impossible, to use these catheters in the smaller and more tortuous coronary vessels. The second of these disadvantages is torquability of the known catheters. Indeed, the poor responsiveness of the distal end of known catheters to rotational inputs applied at the proximal end (this poor response being referred to herein as a high torque ratio, a superior response being referred to herein as low torque ratio) is the result of the elliptical cross-sectional shape of their catheter shafts. This renders the manipulation, correct placement and orientation of the distal end of the catheter device within the patient's vessels difficult. Known atherectomy catheters are also limited in the amount of atheroma tissue they can retrieve. This is due, in part, to the low cut tissue storage capacity of known nose cones.

Balloon-based catheter stabilization systems also have a number of drawbacks. The most important of these is that, in some applications, the balloon tends to slip into the area of the vessel from which a portion of atheroma was just cut. This is because, when atheroma is cut, it creates a low area, or depression relative to the remainder of the occlusion. The balloon, by virtue of its shape and texture, naturally tends to slip into that area. This can render the proper positioning of the housing window or opening difficult. Moreover, conventional balloon-based catheters can only be inflated to a predetermined diameter. This limits their application to a specific vessel lumen diameter.

There have been a number of mechanical stabilization systems proposed, notably based upon complicated structures or shape memory metals which alter their shape when a current is applied to them. These are disclosed in Conley et al., U.S. Pat. No. 5,527,325 and Klein et al., U.S. Pat. No. 5,279,565, the specifications of which are incorporated by reference. However, these suffer from undue complexity and high cost of manufacture.

SUMMARY OF THE INVENTION

It is, therefore, an object of the present invention to provide an over-the-wire catheter device of small size and substantially circular cross section.

It is another object of the present invention to provide a catheter with improved maneuverability.

It is an additional object of the present invention to provide a catheter having improved torquability.

It is an additional object of the present invention to provide an alternative to balloon-based catheter stabilization systems.

In accordance with the above objects and those that will be mentioned and will become apparent below, the over-the-wire catheter device for use in a biological conduit according to the present invention comprises:

a substantially round housing torque cable having a proximal end and a distal end;

a housing connected to the distal end of the housing torque cable, the housing including a window for invaginating biological tissue;

a cutter torque cable, the cutter torque cable being concentric with the housing torque cable;

a cutter movably attached to a distal end of the cutter torque cable to operate within the housing, the window exposing the cutter;

a guidewire concentrically disposed within the cutter torque cable and the cutter;

a balloon disposed opposite the window; and a balloon inflation lumen disposed inside the housing torque cable and emerging outside the housing torque cable adjacent the proximal end of the housing to provide fluid communication with the balloon.

An advantage of this embodiment is that the positioning of the catheter within the biological vessel is facilitated by disposing the balloon inflation lumen and the cutter torque cable within the housing torque cable.

According to an exemplary embodiment, the nose cone comprises at least one longitudinal or wire-reinforced rib for strengthening the nose cone. An advantage of this embodiment is that the at least one longitudinal rib increases the nose cone's column strength and torsional strength. The nose cone may be made of nylon or polyurethane. According to another exemplary embodiment, the nose cone may have a cylindrical shape over at least 70% of its length, the nose cone thereafter tapering toward its distal end. An advantage of this exemplary embodiment is that the cylindrical shape allows a large volume of atheroma to be stored in the nose cone. To facilitate positioning the catheter within the biological conduit, the nose cone is marked with barium or with other radio-opaque material. In an exemplary embodiment of the present invention, the housing is made from at least one material selected from the group consisting of steel, ceramic, THERMAT, titanium and zirconium.

In another exemplary embodiment, the catheter device for use in a biological conduit according to the present invention comprises:

A substantially round housing torque cable having a proximal end and a distal end;

a housing connected to the distal end of the housing torque cable, the housing including a window for invaginating biological tissue;

a cutter torque cable concentrically disposed within the housing torque cable;

a cutter movably attached to a distal end of the cutter torque cable to operate within the housing, the window exposing the cutter;

a nose cone for collecting and storing atheroma cut by the cutter;

a resilient stabilizing member disposed outside and opposite the housing window, the stabilizing member having a proximal end and a distal end, the distal end of the stabilizing member being attached to a distal end of the housing, and a stabilizing cable for selectively bowing and flattening the stabilizing member, the stabilizing cable being disposed within a cable lumen running within the housing torque cable and emerging adjacent a proximal end of the housing to allow the stabilizing cable to connect to the proximal end of the stabilizing member. When the stabilizing cable is advanced in a distal direction, the stabilizing member bows away from the housing to stabilize the catheter housing within the biological conduit, and when the stabilizing cable is retracted in the proximal direction, the stabilizing member flattens about the housing to allow free movement of the catheter housing within the biological conduit. This stabilizes the catheter according to the present invention without the use of an inflatable balloon.

The present invention is also a system for stabilizing a catheter within a biological conduit, the catheter having a proximal end and a distal end, the catheter further having a housing disposed at the distal end of the device, the housing including a window exposing a work element. The system comprises:

a resilient stabilizing member disposed outside and across the housing of the catheter, the stabilizing member having a proximal end and a distal end, the distal end of the stabilizing member being attached to a distal end of the housing, and a stabilizing cable for selectively bowing and flattening the stabilizing member, the stabilizing cable being disposed within a cable lumen within the catheter, the cable lumen emerging adjacent a proximal end of the housing to allow the stabilizing cable to connect to the proximal end of the stabilizing member. When the stabilizing cable is advanced in a distal direction, the stabilizing member bows away from the housing and against the biological conduit to stabilize the housing, and when the stabilizing cable is retracted in a proximal direction, the stabilizing member flattens about the housing to allow free movement of the device within the biological conduit.

According to an exemplary embodiment, the resilient stabilizing member is a thin strip of relatively hard, resilient material. This material may be, for example, stainless steel, polycarbonate or polyimide. According to an exemplary embodiment, the resilient stabilizing member is disposed outside the housing about 180 degrees away from the housing window.

BRIEF DESCRIPTION OF THE DRAWING

For a further understanding of the objects and advantages of the present invention, reference should be had to the following detailed description, taken in conjunction with the accompanying drawing, in which like parts are given like reference numerals and wherein:

FIG. 1 shows an embodiment of an over-the-wire atherectomy catheter according to the present invention.

FIG. 2 shows a cross section of the over-the-wire atherectomy catheter of FIG. 1, taken along line A—A.

FIG. 3 shows another embodiment of the over-the-wire atherectomy catheter, including a mechanical tissue invagination stabilizing system.

FIG. 4 shows a detail of a top view of the mechanical tissue invagination stabilizing system shown in FIG. 3.

DETAILED DESCRIPTION OF THE INVENTION

Referring now to FIGS. 1 and 2, an over-the-wire atherectomy catheter according to the present invention is shown generally at 100.

Figure 5:
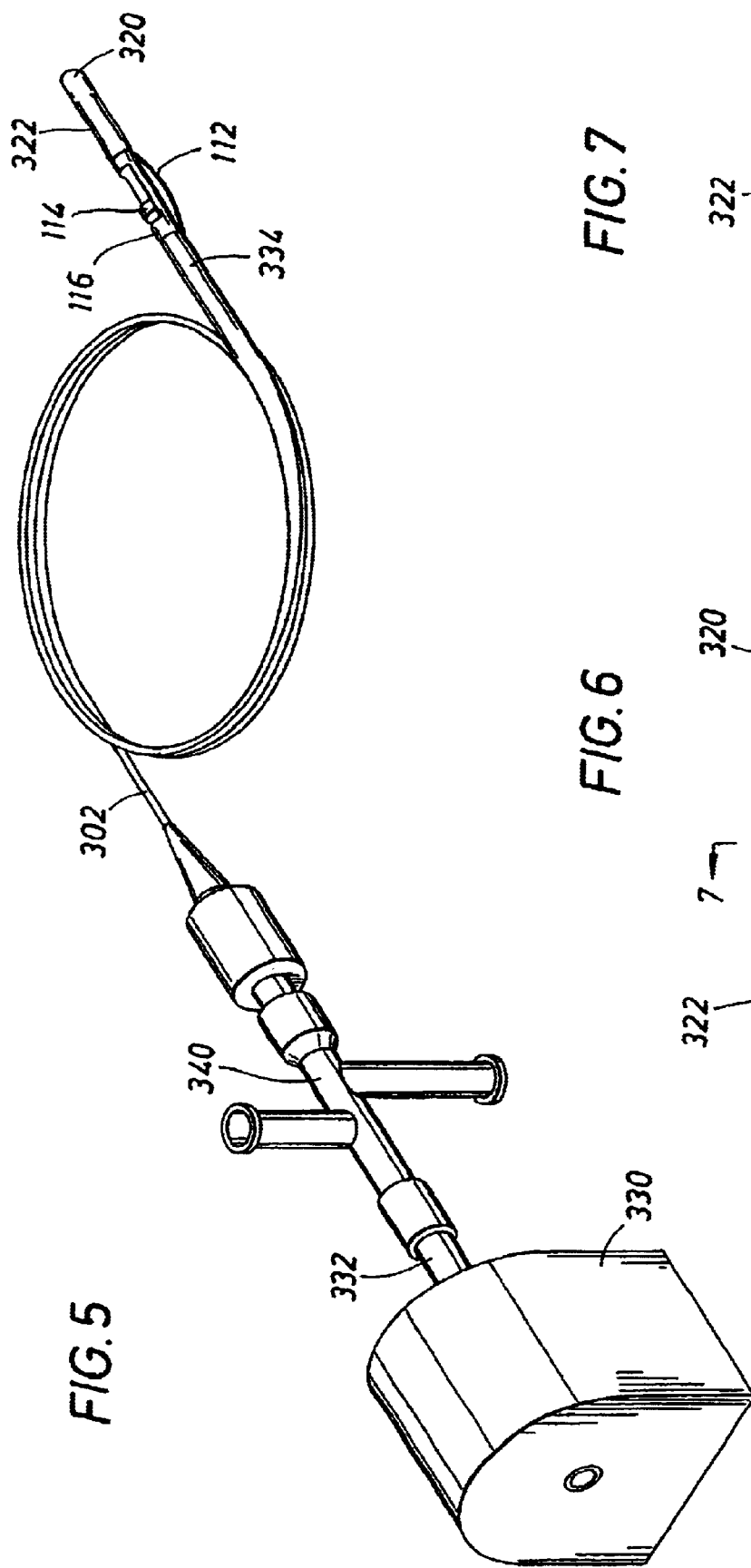
FIG. 5 shows an atherectomy catheter assembly, including the Motor Drive Unit, according to the present invention.

The catheter device according to the present invention includes a substantially round Housing Torque Cable 102, or HTC 102. The HTC 102 runs from the Motor Drive Unit (MDU) 330 at its proximal end 332 to the housing 116 at the distal end 334 of the HTC 102, as shown in FIG. 5. The Cutter Torque Cable 104, or CTC 104, is a braided stainless steel flat wire which is attached, at its proximal end, to the MDU 330 and to a work element, such as cutter 114 at its distal end. The MDU 330 rotates the CTC 104, and thus rotates the work element 114 at a high rate of speed, such as 2,000 rpm (revolutions per minute). The cutter 114 is also adapted to undergo a reciprocal movement along the longitudinal axis 115 of the catheter device 100, guided and constrained by the interior walls of the housing 116. The work element 114 may also be an imaging device, such as an ultrasonic transducer, or a combination of an imaging device and a cutter. A window 122 in the housing 116 exposes the work element, such as the cutter 114. The window 122 operates to invaginate biological tissue (not shown), where it can be cut by the cutter 114.

The HTC 102 is substantially round and the CTC 104 is concentric therewith. A guidewire 120 is concentric with the CTC 104 and the cutter 114, running down the longitudinal axis 115 thereof. The entire catheter device 100, therefore, runs over the guidewire 120 during placement thereof in the biological conduit of the patient. Once in the intended position, for example facing an atheroma, the guidewire 120 may be distally retracted, leaving the catheter device 100 in place for tissue cutting and retrieval.

A balloon 112 having a proximal end 108 is disposed externally to the housing 116 and is oriented 180 degrees from the housing 116. The balloon 112, when inflated, stabilizes the catheter device 100 within the biological vessel (not shown), such as an artery. To inflate the balloon 112, it is necessary to introduce an inflation fluid therein, under pressure. This is done, in the present invention, by means of inflation lumen 106 through the proximal end 108. Inflation lumen 106 is disposed within the HTC 102, as shown in FIGS. 1 and 2. That the inflation lumen 106 is contained within the concentric HTC 102, and not outside it, greatly facilitates the positioning of the catheter device 100 in the biological conduit. This is because disposing the balloon inflation lumen 106 within the HTC 102 contributes to a low torque ratio, as the profile of the HTC 102 remains substantially round, as shown in FIG. 2. In conventional catheters, high torque ratios resulted from their elliptical cross-sectional shape. This elliptical cross-sectional shape was partly due to inflation lumens that were disposed external to the housing torque cable. This resulted in difficulties in manipulating and orienting the housing/cutter mechanism. In the present invention, however, manipulation and orientation of the catheter device 100 is facilitated by disposing the CTC 104 concentric with the HTC 102 and by disposing the inflation lumen 106 within the HTC 102.

The inflation lumen 106 is connected to the balloon 112 through the proximal end 108 and a leg 110 of the balloon 112. The balloon inflation lumen 106 emerges from within the HTC 102 at the balloon leg 110, adjacent the proximal end of the housing 116 to provide fluid communication with the balloon 112.

Another embodiment of the present invention is shown in FIGS. 3 and 4. Elements of FIGS. 3 and 4 which are similar to the corresponding elements of FIGS. 1 and 2 have been given like reference numerals. A detailed description of these like elements, therefore, will be omitted for the sake of brevity.

Figure 7:
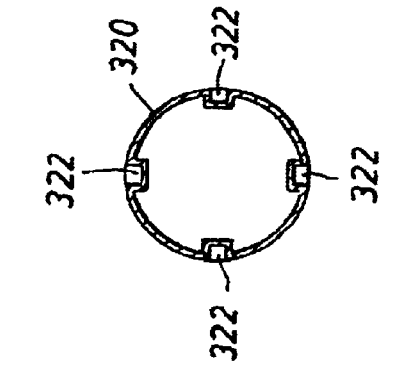
FIG. 7 shows a cross-section of the nose cone of FIG. 6, taken along line A—A.
Figure 6:
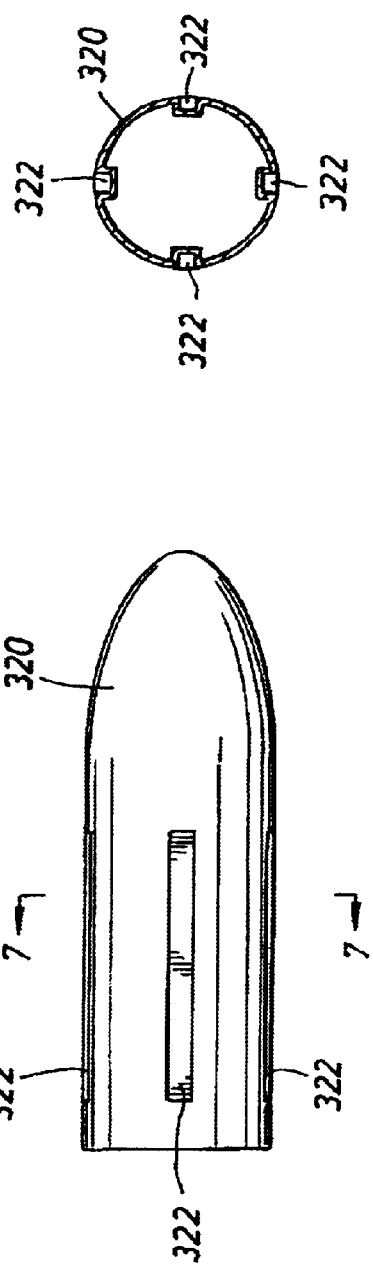
FIG. 6 shows an embodiment of the nose cone according to the present invention.

The embodiment of FIGS. 3 and 4, shown generally at 300, comprises a mechanical tissue invagination stabilizing system. FIGS. 3 and 4 show a portion of a nose cone 320, whereas FIG. 6 shows a complete nose cone 320 according to the present invention. The nose cone according to the present invention comprises at least one longitudinal or wire-reinforced rib 322 for strengthening the nose cone by increasing its column strength and torsional strength characteristics. FIG. 7 shows a cross-section of the nose cone 320 of FIG. 6, taken along line A—A. In FIG. 7, four longitudinal ribs 322 are visible. As the nose cone 320 comprises at least one strengthening longitudinal rib 322, it does not require, and does not comprise, a coiled spring therein, as in conventional nose cones. However, the number of such longitudinal ribs 322, as well as their length and shape, may be varied at will, consistent with the goals of increasing column strength and torsional strength of the nose cone 320 with or without resorting to a coiled inner nose cone ring to provide the desired strength and flexibility characteristics. As the nose cone 320 according to the present invention does not comprise a coiled spring, the interior volume thereof, which is available for tissue storage, is increased relative to known nose cones. The nose cone 320 may be made of nylon or polyurethane. Unlike conventional nose cones which taper along their entire length, the nose cone 320 according to the present invention has a cylindrical shape over at least 70% of its length, and tapers only at its distal-most end. This substantially cylindrical shape over at least 70% of its length allows the nose cone 320 according to the present invention to store a larger volume of cut atheroma than was previously possible. To make the nose cone 320 according to the present invention visible under fluoroscopy, it is marked with barium, or another radio-opaque material which is highly visible during fluoroscopy. This, in turn, facilitates the positioning of the over-the-wire catheter according to the present invention.

To increase the amount of atheroma tissue retrieved, however, is not simply a matter of increasing the capacity of the nose cone 320. What is required is the ability to invaginate a greater amount of tissue. This is done, in the present invention, by constructing the housing 116 of the catheter according to the present invention from stronger, stiffer materials. This produces a more rigid housing. A more rigid housing 116, in turn, allows the window 122 to be increased in size. If the window 122 is increased in size, a larger cut may be made by the cutter 114, which increases the usefulness and efficiency of the catheter device. Titanium, Zirconium, 440 Steel, ceramics or Thermat® may be used as the material for the housing 116. These materials allow the housing 116 to exhibit less flexibility and allow the window 122 of the housing 116 to be made larger than was previously possible with conventional catheter housings.

In FIGS. 3 and 4, instead of the assembly consisting of the inflation lumen 106 and balloon 112, as shown in FIGS. 1 and 2, a stabilizing member cable 308 and resilient stabilizing member 312 are employed. The resilient stabilizing member 312 is made of an elastic material, such as stainless steel, or a shape memory metal, such as NITINOL. The resilient stabilizing member 312 is attached, at its distal end, to the nose cone 320 or, alternatively, to the distal end of the housing 116. The resilient stabilizing member 312 is disposed outside of the housing 116 and approximately 180 degrees away from the window 122 in the housing 116.

The proximal end of the resilient stabilizing member 312 is attached to a stabilizing cable 308 running within a cable lumen 306. The cable lumen 306 runs within the HTC 102 from the proximal end of the HTC 102 to the distal end of the HTC 102. The cable lumen 306 emerges at orifice 310, adjacent the proximal end of the housing 116. The resilient stabilizing member 312 attaches to the stabilizing member cable 308 inside the cable lumen 306.

FIG. 4 is a plan view of the catheter device 300 according to the present invention. FIG. 4 shows the resilient stabilizing member 312 disposed between the nose cone 320 and the stabilizing cable 308. The resilient stabilizing member 312, in an exemplary embodiment of the present invention, comprises a thin strip of resilient material. The width of the resilient stabilizing member 312 is at most equal to the width of the catheter device 300 itself, so as not to impede the catheter's progress through the biological conduits, such as the patient's arteries. As clearly shown in FIG. 4, the proximal end of the resilient stabilizing member 312 is attached to the stabilizing member cable 308, whereas the distal end thereof is attached to the proximal end of the nose cone 320 or, alternatively, to the distal end of the housing 116.

In one exemplary embodiment, the resilient stabilizing member 312 comprises a thin strip of resilient material having a substantially rectangular center portion, a distal end thereof tapering to its attachment point at the proximal end of the nose cone 320 or the distal end of the housing 116, and a proximal end thereof tapering and attaching to the stabilizing member cable 308.

The mechanical tissue invagination stabilizing system shown in FIGS. 3 and 4 operates as follows. When the catheter 300 is advanced within a biological conduit to an area of interest, such as an atheroma site, the stabilizing cable 308 is advanced in the distal direction. This causes the resilient stabilizing member 312, being anchored at its distal end, to bow away from the housing 116 and against the artery walls or the atheroma. This pushes the window 122 up against the opposing wall, thus forcing atheroma inside the window 122 of the housing 116, where it is cut by cutter 114. The degree of bowing of the resilient stabilizing member 312 is controlled by the amount of advancement of the stabilizing cable 308 in the distal direction; the degree of bowing of the resilient stabilizing member increases as the stabilizing cable 308 is advanced in the distal direction. Conversely, when the stabilizing cable 308 is retracted in the proximal direction, the stabilizing member 312 flattens to and about the housing 116, to allow free movement of the catheter device 300 within the biological conduit.

Unlike fluid filled balloons which can only expand to a predetermined size or diameter, the mechanical tissue invagination system according to the present invention can be smoothly expanded over a great range, and is not limited to a predetermined expansion limit, as is the case with balloon-based catheter stabilization systems.

In the present invention, the degree of bowing or flattening of the resilient stabilizing member 312 is controlled by the distance that the stabilizing cable 308 is advanced or retracted, respectively. The physician, therefore, has much greater control over the amount of force exerted by the stabilizing system onto the atheroma or artery walls than is the case with balloon-based stabilizers.

It is an advantage of this embodiment of the present invention to provide added stability of the catheter during use, as compared to conventional balloon-based stabilizers. Indeed, the rounded profile of balloons causes the housing/balloon assemblies to undesirably rotate until the balloon is seated in the lowest portion of the arterial lumen. For example, once atheroma tissue has been cut by the cutter of the catheter, conventional balloons have a tendency to slip into the area that was just cut, the lowest portion of the atheroma site. The mechanical tissue invagination stabilizing system according to the present invention overcomes this tendency, as the resilient stabilizing member 312 is generally flat. This flat surface is much less likely to slide into the low portions of the atheroma site, and is more likely to maintain the position and orientation intended by the treating physician.

While the foregoing detailed description has described several embodiments of this invention, it is to be understood that the above description is illustrative only and not limiting of the disclosed invention. For example, the shape of the resilient stabilizing member may be varied from that described and shown in the drawings. Other modifications will no doubt occur to those of ordinary skill, and all such modifications are deemed to fall within the scope of the claims. Thus, the invention is to be limited only by the claims as set forth below.

What is claimed is:

1. A catheter comprising:
   a housing torque cable having a proximal end and a distal end, said housing torque cable having an inflation lumen therein;
   a housing connected to the distal end of the housing torque cable, the housing including a window for invaginating biological tissue;
   a cutter torque cable located within the housing torque cable;
   a cutter attached to a distal end of the cutter torque cable and within the housing, the window exposing the cutter;
   a balloon disposed opposite the window, said balloon coupled to said inflation lumen; and
   a nose cone coupled to a distal end of said housing, the nose cone including at least one longitudinal rib embedded in an outer wall of the nose cone, the at least one longitudinal rib increasing column strength and torsional strength of the nose cone.

2. A catheter according to claim 1, wherein the nose cone is made of a polymer chosen from the group consisting of nylon and polyurethane.

3. A catheter according to claim 1, wherein the nose cone has a length and a cylindrical shape over at least 70% of said length and tapering towards a distal end.

4. The catheter according to claim 1, wherein the nose cone is marked with barium and is visible during fluoroscopy to facilitate positioning the catheter within a biological conduit.

5. A catheter according to claim 1, wherein the housing is made from at least one material selected from the group consisting of steel, ceramic, titanium and zirconium.

6. A catheter comprising:
   a housing torque cable;
   a housing connected to a distal end of the housing torque cable, the housing including a window for invaginating biological tissue;
   a cutter torque cable disposed within the housing torque cable;
   a cutter attached to a distal end of the cutter torque cable to operate within the housing, the window exposing the cutter;
   a nose cone coupled to a distal end of the housing for collecting and storing atheroma cut by the cutter;
   a resilient stabilizing member having a flat surface to stabilize a portion of the catheter within a biological conduit when positioned therein, the resilient stabilizing member disposed outside and opposite the housing window; and
   a stabilizing cable coupled to said resilient stabilizing member for selectively bowing and flattening the stabilizing member, wherein the resilient stabilizing member is taperingly attached to a distal end of the housing and the resilient stabilizing member is taperingly coupled to the stabilizing cable.

7. A catheter according to claim 6, wherein the nose cone comprises at least one longitudinal rib for strengthening the nose cone, the at least one longitudinal rib being disposed embedded in an outer wall of the nose cone.

8. A catheter according to claim 6, wherein the nose cone is made of a material selected from a group consisting of nylon and polyurethane.

9. A catheter according to claim 6, wherein the nose cone has a cylindrical shape over at least 70% of a length of the nose cone, the nose cone tapering towards distal end.

10. A catheter according to claim 6, wherein said nose cone is marked with barium and visible during fluoroscopy to facilitate positioning the catheter within the biological conduit, said nose cone coupled to a distal end of the housing for collecting and storing atheroma cut by the cutter.

11. A catheter according to claim 6, wherein housing is made from at least one material selected from a group consisting of steel, ceramic, titanium and zirconium.

12. A catheter comprising:
a housing having a window;
a work element within said housing and exposed by said window;
a resilient stabilizing member across a portion of said housing opposite said window, said resilient stabilizing member including a flat surface to contact a wall of a biological conduit to avoid rotational slip of said housing when placed within said biological conduit; and
a stabilizing cable through a lumen of said catheter and coupled to said resilient stabilizing member to selectively effect said flat surface to contact said wall of said biological conduit, the resilient stabilizing member being taperingly coupled to the stabilizing cable and the resilient stabilizing member being taperingly attached to a distal end of the housing.

13. A catheter according to claim 12, wherein the resilient stabilizing member is a thin strip of resilient material.

14. A catheter according to claim 12, wherein the resilient stabilizing member is a thin strip of resilient material selected from a group consisting of stainless steel, a nickel-titanium alloy, and titanium.

15. A catheter according to claim 12, wherein the housing is made from at least one material selected from a group consisting of steel, ceramic, titanium, and zirconium.

16. A catheter according to claim 12, wherein the resilient stabilizing member comprises:
a proximal end;
a distal end; and
a substantially plat center portion, the substantially flat center portion having a width substantially equal to a width of the housing, wherein the substantially flat center portion taperingly extends to the proximal end and the substantially flat center portion taperingly extends to the distal end.

17. A catheter according to claim 12, wherein the resilient stabilizing member is a thin strip of resilient material, the material being selected from the group consisting of polycarbonate and polyamide.

18. A catheter comprising:
a housing torque cable having a proximal end and a distal end, said housing torque cable having a inflation lumen therein;
a housing connected to the distal end of the housing torque cable, the housing including a window for invaginating biological tissue;
a cutter torque cable located within the housing torque cable and to accommodate a guidewire, the cutter torque cable being concentric with the housing torque cable;
a cutter attached to a distal end of the cutter torque cable and within the housing, the window exposing the cutter;
a balloon disposed opposite the window, said balloon coupled to said inflation lumen; and
a nose cone coupled to a distal end of said housing and including at least one longitudinal rib to increase strength of the nose cone, the at least one longitudinal rib being disposed embedded in an outer wall of the node cone.

19. A catheter nose cone, comprising an open proximal end, a tapered distal end and a substantially cylindrical body therebetween, a nose cone length being defined as the longitudinal distance from the proximal end to the distal end;
the proximal end being attachable to a catheter;
the body having a length at least approximately 70% of the nose cone length;
the body including at least one longitudinal rib, the at least one longitudinal rib being disposed embedded in an outer wall of the body.

20. The catheter nose cone of claim 19 comprised of a material selected from he group consisting of nylon and polyurethane.

21. The catheter nose cone of claim 19 wherein the catheter nose cone is marked with barium to facilitate positioning within a biological conduit.

22. The catheter nose cone of claim 14 wherein the catheter nose cone is coupled to a housing of said catheter, said housing to be stabilized within a biological conduit by a resilient stabilizing member of said catheter, said resilient stabilizing member comprising:
a proximal end;
a distal end; and
a substantially plat center portion, the substantially flat center portion having a width substantially equal to a width of the housing of the catheter, wherein the substantially flat center portion taperingly extends to the proximal end and the substantially flat center portion taperingly extends to the distal end.

\* \* \* \* \*

UNITED STATES PATENT AND TRADEMARK OFFICE
CERTIFICATE OF CORRECTION

PATENT NO.   : 6,645,217 B1
DATED        : November 11, 2003
INVENTOR(S)  : MacKinnon et al.

It is certified that error appears in the above-identified patent and that said Letters Patent is hereby corrected as shown below:

Column 10,
Line 44, delete "claim 14" and insert -- claim 19 --.

Signed and Sealed this

Twenty-seventh Day of April, 2004

JON W. DUDAS
*Acting Director of the United States Patent and Trademark Office*